United States Patent [19]

Lübbers

[11] 4,272,484
[45] Jun. 9, 1981

[54] FILLING FOR OPTODES

[75] Inventor: Dietrich W. Lübbers, Dortmund, Fed. Rep. of Germany

[73] Assignee: Max-Planck-Gesellschaft zur Forderung der Wissenschaften e.V., Goettingen, Fed. Rep. of Germany

[21] Appl. No.: 72,780

[22] Filed: Sep. 5, 1979

[30] Foreign Application Priority Data

Dec. 27, 1978 [DE] Fed. Rep. of Germany ....... 2856251

[51] Int. Cl.³ .................... G01N 21/78; G01N 21/64
[52] U.S. Cl. .................................. 422/68; 23/230 B; 356/246; 356/441; 422/58; 422/50; 435/299
[58] Field of Search ............ 23/232 R, 232 E, 230 B; 422/57, 52, 55, 86, 91, 68, 58, 50; 356/39, 85, 246, 436, 441; 204/19 SM, 19 P

[56] References Cited

U.S. PATENT DOCUMENTS

| 3,404,962 | 10/1968 | Medlar et al. | 422/86 |
| 3,572,994 | 3/1971 | Hochstrasser | 23/232 R |
| 3,754,867 | 8/1973 | Guenther | 23/232 R |
| 4,003,707 | 1/1977 | Lubbers et al. | 23/232 R |

Primary Examiner—Ronald Serwin
Attorney, Agent, or Firm—Michael J. Striker

[57] ABSTRACT

In order to improve the selectivity of an indicator chamber or optode consisting of an indicator and a membrane impermeable to the indicator and surrounding it, for use in the measurement of concentration of component particles by means of an optical light measurement system including a light source, a light receiver and a readout device, a substance which reacts with the particle to be measured is provided within the indicator chamber, and the reaction product then modifies the optical properties of the indicator.

13 Claims, 3 Drawing Figures

FILLING FOR OPTODES

BACKGROUND OF THE INVENTION

The invention concerns an indicator chamber (optode) comprising an indicator and a membrane surrounding the indicator and impermeable to it for measurement of concentrations of substance particles by means of e.g. a light measurement system, such as a light source, light receiver and readout means. In particular, the invention concerns the material used for filling the optode.

The known systems operate on the principle that the portion of a composition to be measured in separated from components which disturb the accuracy of measurement. If, for example, the oxygen content of blood is to be determined through fluorescence methods, certain protein fractions would render the direct readings inaccurate due either to their own fluorescence or through binding of the indicator. Through separation of the measurement area by means of a membrane, through which the fraction to be measured diffuses, the blood protein fractions and other components are held back, thereby preventing their affecting the accuracy of measurement.

A disadvantage of these systems lies in the fact that the indicators used are not terribly selective, and thus would react with other components than that to be measured, or in that no species-specific indicators are available. In this, the applicability of the method is restricted. This is in particular unfortunate, in that the method employed requires a lower level of the component to be measured than other methods, and in addition is robust and directly applicable without preparation. With respect to the nature and operation of the optodes, the entire teachings of U.S. Pat. No. 4,003,707 are hereby incorporated by reference.

SUMMARY OF THE INVENTION

It is, therefore, an object of the invention to prepare fillings for optodes, which are selective for the particular component particle to be measured and which would be suitable for the broadest range of particle types.

This object is achieved by providing in the filling for the optode a substance which reacts with the component particles to be measured; a reaction product is produced which then alters the optical properties of the indicator.

The advantage of the arrangement lies in the fact that the reacting substance can be matched quite closely to the indicator, the transport properties of the membrane and the particle to be measured. For example, if for the measurement of hydrogen ions, acetic acid is used as reacting substance and $\beta$-methyl-umbelliferon as indicator than with the hydrogen ion indicator, anions can also be measured indirectly since for every hydrogen ion one anion is freed. Further, through the use of a selectively reacting substance a known indicator can in effect be transformed into one for another type of particle. For dynamic use it is necessary that the reaction be reversible.

A very high selectivity may be achieved if the reacting substance used is an enzyme, as enzymes generally only react with a single specific substance, while the reaction products, such as hydrogen ions, oxygen, etc. are easily detectable through the use of known indicators, such as $\beta$-methyl-umbelliferon and pyrenebutyric acid.

As membranes come into consideration porous membranes which in themselves are only slightly selective. This difficulty is overcome through the specificity of the reaction itself.

Certain enzymatic reactions are of particular significance in this context. Thus, a measurement of glucose through optodes with porous hydrophobic membranes is convenient with a filling of glucose oxydase and pyrenebutyric acid for glucose concentration determinations through fluorescence. Through placement of optode capsules in tissue near the skin a simple monitoring of the blood sugar level, for example in intensive care stations, may be carried out. For this, suitable light wave lengths are used which easily permeate the skin, such as infra-red light.

To strengthen the measurement signal it is possible to provide a substance which binds with the particle to be measured, as the equilibrium of that particle component in the interior of the optode is thereby shifted.

In another embodiment of the invention, the reacting substance is an antibody. This also permits a tremendous increase in the specificity of the optode, as antibody-antigen reactions are highly specific. A chromophore as indicator may be chemically affixed to the antibody.

As membranes with relatively large pores are used for the large particles which, for example, react with antibodies or enzymes, it is desirable in order to avoid the draining out of indicator, antibodies or enzyme, to fix these substances. This may be carried out in conventional manner.

When the reacting substance for the transmission of a particle to be measured to an indicator is not very selective, the selectivity of the optode may be improved through the use of a selectively-working membrane provided with a carrier. This type of arrangement also leads to a broadening of the range of applicability of the optode. Substances, known as ligands, may be dissolved in solid or liquid membranes and are able to form complexes with the particles to be measured; in most cases, the substances completely surround the particle. Cf., e.g., J. Koryta, Ion-selective Electrodes, Cambridge (1975). It is possible to synthesize such carrier especially designed for a particular type of particle, so that the selectivity can be quite high, while the range of possible applications includes a virtually limitless number of particle types. An example of such a separation pair is the antibiotic valinomycin and K+ ions; the carrier may be dissolved in PVC. See Res. Devel. 25:20-24 (1974); J. Amer. Chem. Soc. 89: 386 (1967).

The selectivity can be further heightened through the use of a multiple membrane around the optode. In such an arrangement, membranes with diverse carriers can be used one after the other, such membranes in general having the highest permeability for the particle component to be measured but a low permeability for other components.

A further improvement may be achieved through providing an indicator chamber within a second indicator chamber which encases it, as thereby one membrane may possess one type of property and the second another. For example, the outer membrane may be glucose permeable, and the reaction with glucose would be carried out by glucose oxidase within the first indicator chamber, while the thus-generated oxygen would diffuse into the second (internal) indicator chamber through the inner membrane and would there undergo the fluorescence reaction with pyrenebutyric acid. In addition, a substance for binding oxygen may be provided in the inner indicator chamber; the binding should be chemically or physically reversible, causing no disturbance of the accuracy of measurement while heightening the oxygen concentration and thus the intensity of the measuring signal. Additionally, a reference indicator can be provided by conventional methods in the inner indicator chamber, with the help of which absolute calibration of the optodes is made possible.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
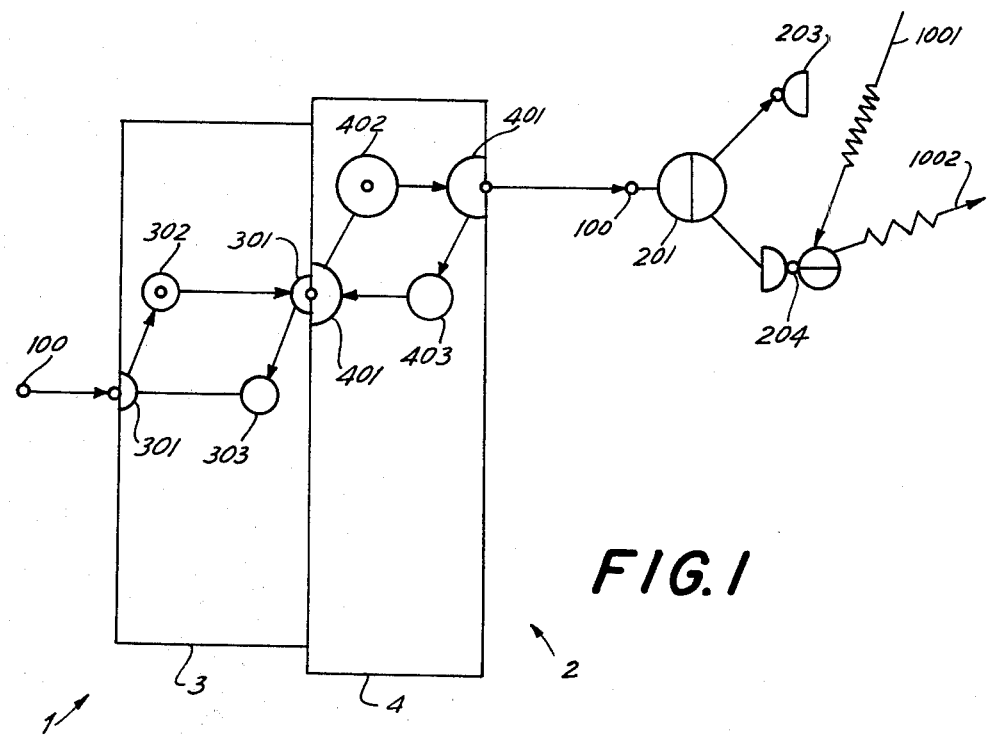
FIG. 1 illustrates the passage of a particle to be measured into, and the reaction within, the optode.

In the embodiment of FIG. 1, a double membrane 3, 4 closes off an indicator chamber 2 from a solution to be measured 1. A particle 100 from the concentration to be measured comes into contact at the membrane border with a carrier 301 ready to take up the particle. The carrier 302 charged with the particle 100 subsequently comes into contact at the border of the second membrane 4 with a carrier 401 ready to take up the particle. The carrier-particle combination 402 wanders to the inner border surface of the membrane 4 and the particle 100 enters the indicator chamber 2. A reacting substance 201 comes together with the particle 100, thereby producing reaction products 203 and 204. The reaction product 204 is optically active, for example, becoming fluorescent or changing its color when in contact with light beam 1001. The resultant radiation 1002 is then measured by a light measurement device, which is not illustrated. The preparation of a membrane provided with a carrier and the chemical affixing of a chromophore onto a reaction partner is known from the literature. In addition, the preparation of micro- and nano-capsules is also known, in which the inventive filling may be used, as in surface optodes. See generally Speiser, in J. R. Nixon, Marcel Dekkar Verlag, New York (1976), page 1 ff.

Figure 2:
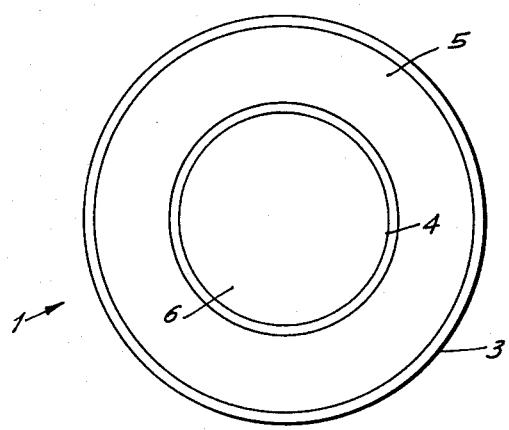
FIG. 2 illustrates a multistage arrangement.

In FIG. 2 a multistage arrangement consisting of an outer membrane 3 and outer reaction chamber 5 as well as an inner membrane 4 and inner reaction chamber 6. If membrane 3 is porous and for the transport of glucose and indicator room 5 filled with a glucose-splitting enzyme immobilized within the indicator chamber, then in chamber 5 oxygen is generated. This can be carried into inner reaction chamber 6 over membrane 4 which is provided with a carrier; the inner chamber 6 in addition to the indicator contains a substance for the binding of oxygen. The fluorescence measurement follows in a known method by means of a light beam for inducing the fluoroescence and a light measurement arrangement, which are not illustrated.

The principle of the invention may be utilized in arrangements with more stages, in which case further encapsulated indicator chambers are comtemplated.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. In an indicator chamber (optode) comprising an indicator and a membrane surrounding said indicator and impermeable to it, for measurement of concentration of particles by means of a light measurement system including a light source, a light receiver and readout means, the improvement comprising providing in a filling within said indicator chamber a substance which reacts with said particle to be measured and which generates through said reaction a reaction product which modifies the optical properties of said indicator, thereby allowing the preparation of highly selective indicator chambers with a broad range of applicability.

2. An optode as defined in claim 1, wherein said substance is an enzyme.

3. An optode as defined in claim 2, wherein said enzyme is glucose oxidase.

4. An optode as defined in claim 1, wherein said substance is an antibody.

5. An optode as defined in claim 1, wherein said membrane consists of more than one layer.

6. An optode as defined in claim 1, wherein said membrane is provided with a carrier for selective transport of said particle to be measured.

7. An optode as defined in claim 1, wherein said substance is fixed into a carrier matrix.

8. An optode as defined in claim 1, wherein said chamber is in the form of a flat surface.

9. An optode as defined in claim 1, wherein said chamber is in the form of a capsule.

10. A optode as defined in claim 1, wherein a first chamber is provided within a second chamber which surrounds it.

11. An optode as defined in claim 10; further comprising additional chambers surrounding said first chamber.

12. An optode as defined in claim 1, wherein a substance which binds said particle to be measured is provided within said chamber.

13. An optode as defined in claim 1, wherein a reference indicator is additionally provided.

* * * * *